(12) United States Patent
Ramachandran et al.

(10) Patent No.: US 8,948,884 B2
(45) Date of Patent: Feb. 3, 2015

(54) HELICAL CORE EAR IMPLANT ELECTRODE

(71) Applicant: MED-EL Elektromedizinische Geraete GmbH, Innsbruck (AT)

(72) Inventors: Anup Ramachandran, Innsbruck (AT); Stefan B. Nielsen, Innsbruck (AT); Claude Jolly, Innsbruck (AT); Martin Zimmerling, Patsch (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 0 days.

(21) Appl. No.: 13/693,268

(22) Filed: Dec. 4, 2012

(65) Prior Publication Data

US 2013/0090711 A1   Apr. 11, 2013

Related U.S. Application Data

(63) Continuation of application No. PCT/US2011/042557, filed on Jun. 30, 2011.

(60) Provisional application No. 61/359,928, filed on Jun. 30, 2010.

(51) Int. Cl.
*A61N 1/05* (2006.01)

(52) U.S. Cl.
CPC .................................. *A61N 1/0541* (2013.01)
USPC ........................................................ 607/137

(58) Field of Classification Search
USPC ............... 607/136–137, 55–56; 600/378–379
See application file for complete search history.

(56) References Cited

U.S. PATENT DOCUMENTS

| 4,573,481 | A | 3/1986 | Bullara | 128/784 |
|---|---|---|---|---|
| 5,964,702 | A | 10/1999 | Grill, Jr. et al. | 600/377 |
| 6,374,143 | B1* | 4/2002 | Berrang et al. | 607/137 |
| 7,085,605 | B2 | 8/2006 | Bluger et al. | 607/116 |
| 7,149,585 | B2 | 12/2006 | Wessman et al. | 607/116 |
| 8,412,342 | B2* | 4/2013 | Zhang et al. | 607/57 |
| 2006/0206185 | A1* | 9/2006 | Schuller | 607/137 |
| 2008/0011721 | A1 | 1/2008 | Park | 219/74 |

(Continued)

FOREIGN PATENT DOCUMENTS

| WO | WO 93/20887 | 10/1993 | A61N 1/04 |
|---|---|---|---|
| WO | WO 2008/011721 | 1/2008 | A61N 1/36 |

OTHER PUBLICATIONS

ISA/US Commissioner of Patents, International Search Report and Written Opinion, PCT/US22/42557, date of mailing Nov. 24, 2011, 9 pages.

*Primary Examiner* — Carl H Layno
*Assistant Examiner* — Paula J Stice
(74) *Attorney, Agent, or Firm* — Sunstein Kann Murphy & Timbers LLP

(57) ABSTRACT

A novel electrode array is described for ear implant systems such as cochlear implants (CI) and vestibular implants (VI). The electrode array includes an electrode array core made of a flexible polymer material including an elongated helical portion having multiple helical turns. Electrode wires are embedded within the array core for carrying electrical stimulation signals. At a terminal end of each electrode wire, an electrode stimulation contact is exposed through the array core for applying the electrical stimulation signals to adjacent neural tissue. An electrode carrier of resilient material encases the electrode array and has an outer surface with contact openings exposing the stimulation contacts.

12 Claims, 11 Drawing Sheets

(56) References Cited

U.S. PATENT DOCUMENTS

| | | | |
|---|---|---|---|
| 2010/0145177 A1 | 6/2010 | Pau et al. | 600/379 |
| 2010/0204768 A1 | 8/2010 | Jolly et al. | 607/137 |
| 2010/0305673 A1 | 12/2010 | Jolly et al. | 607/116 |
| 2010/0305676 A1 | 12/2010 | Dadd et al. | 607/137 |

\* cited by examiner

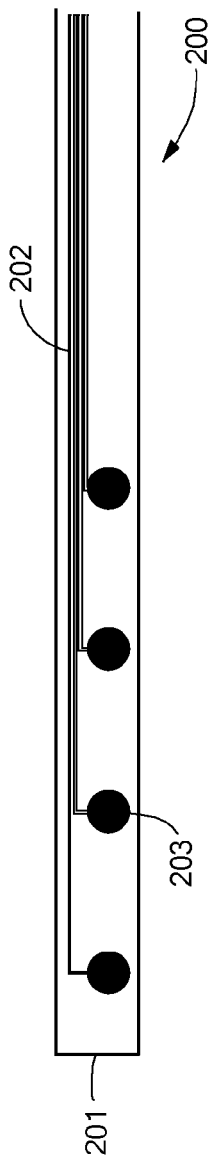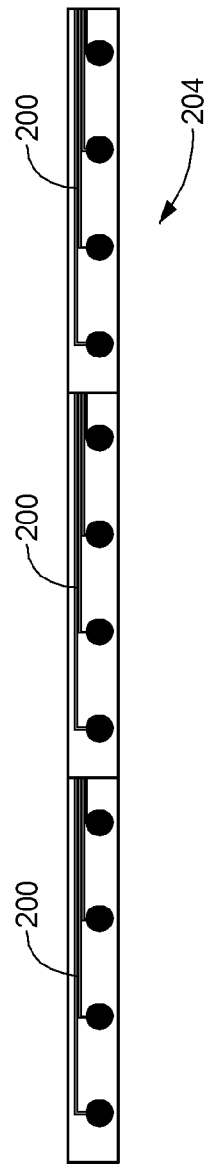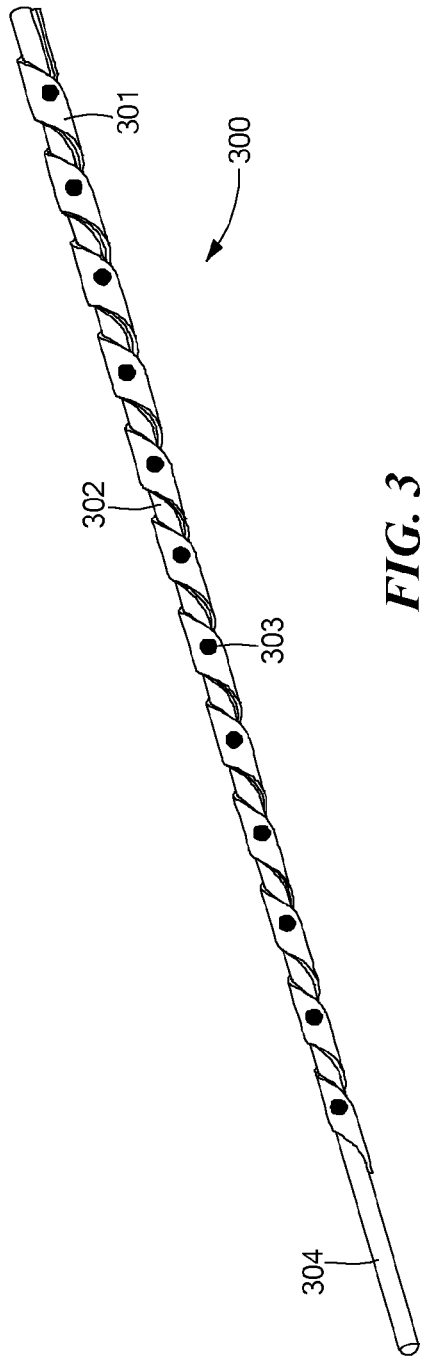

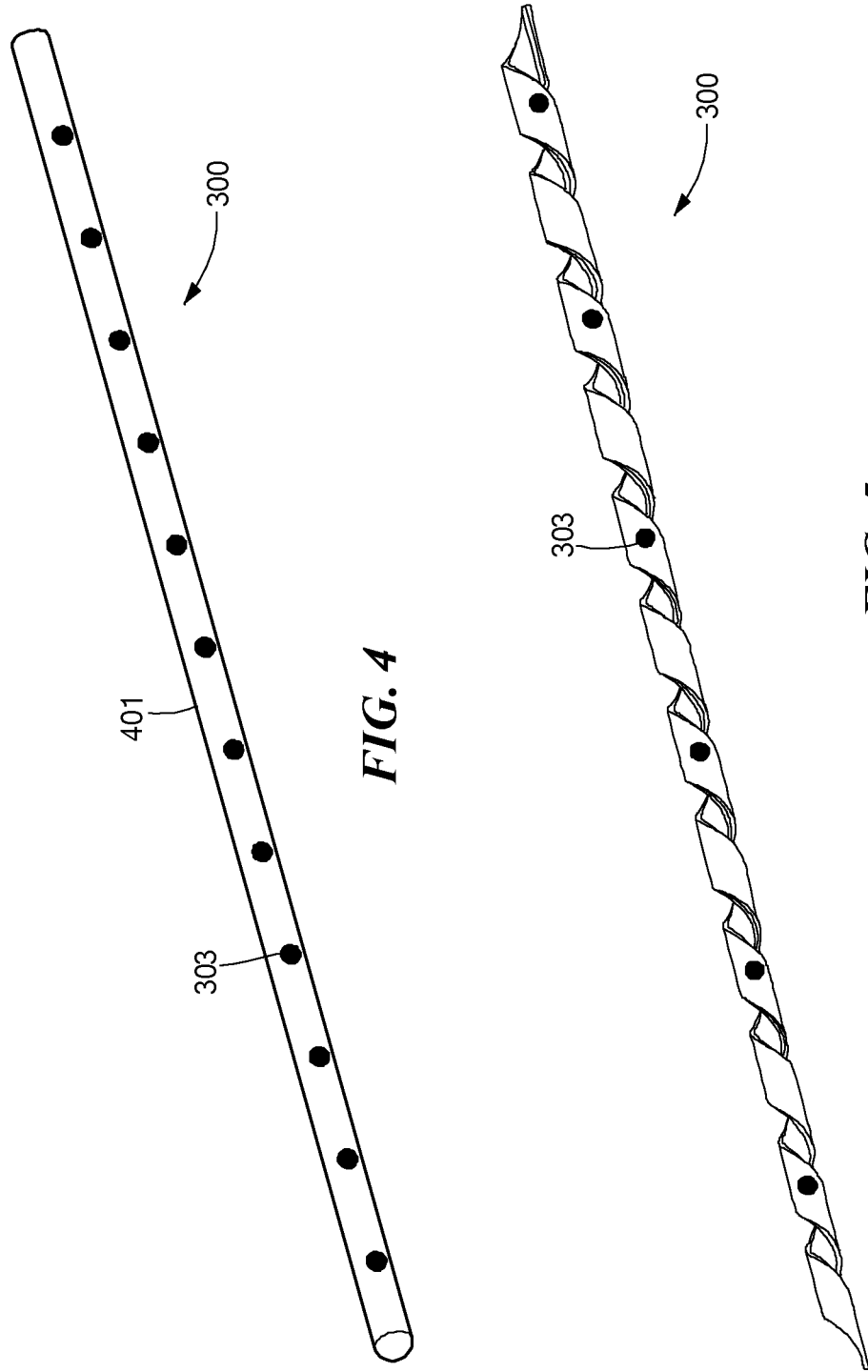

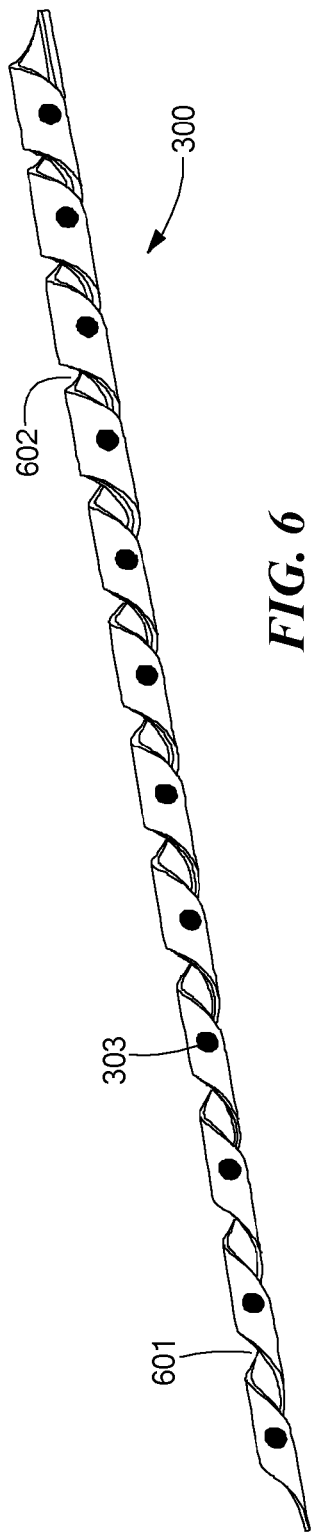
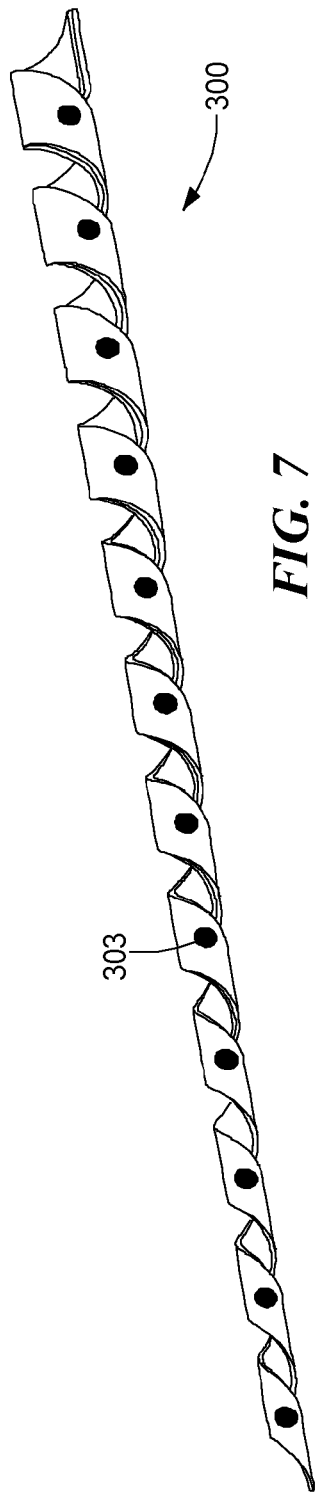
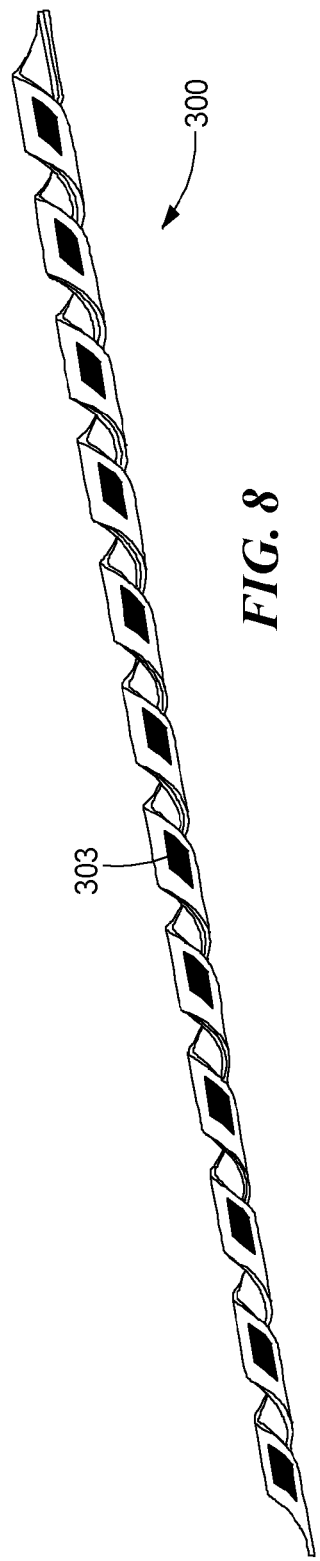
FIG. 6
FIG. 7
FIG. 8

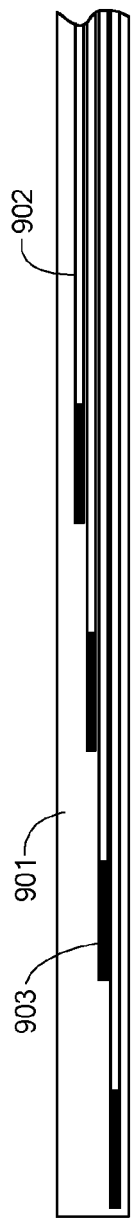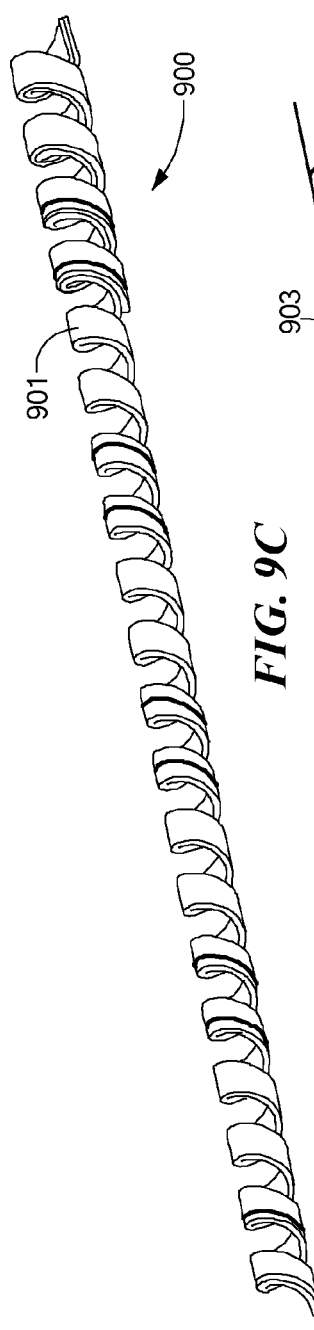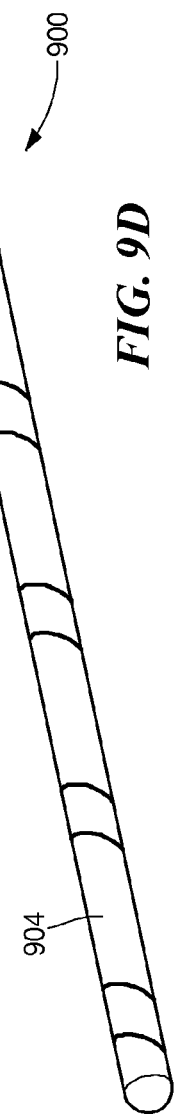
FIG. 9A
FIG. 9B
FIG. 9C
FIG. 9D

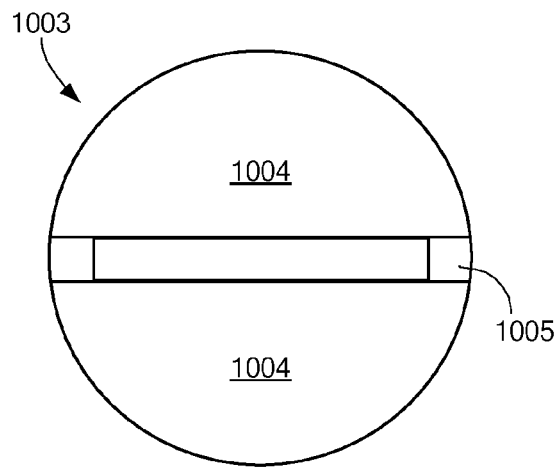
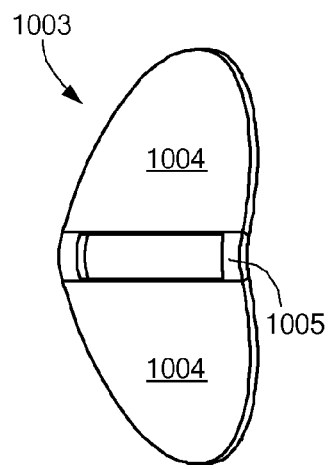
FIG. 10A  FIG. 10B
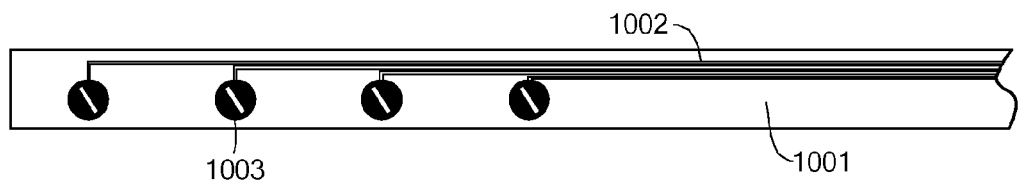
FIG. 10C
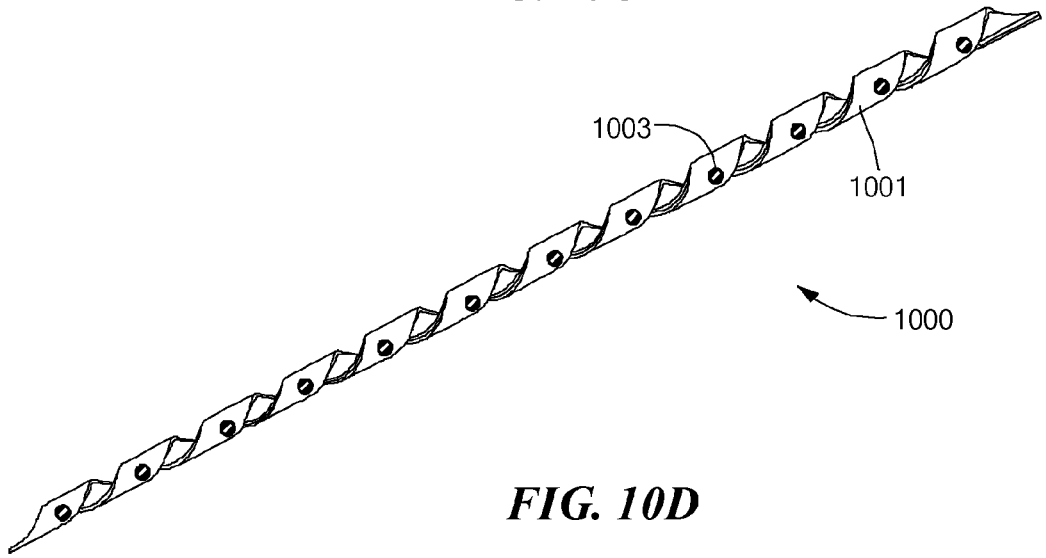
FIG. 10D

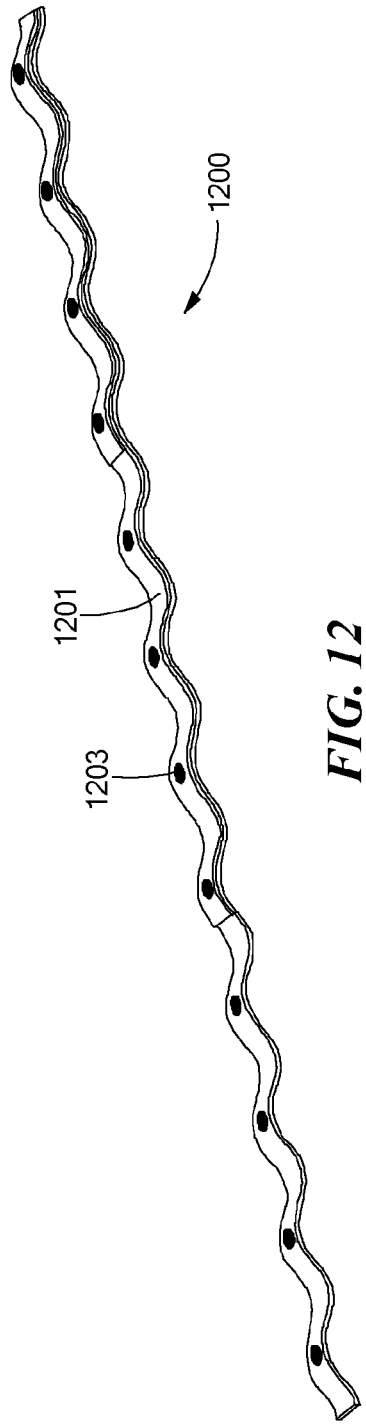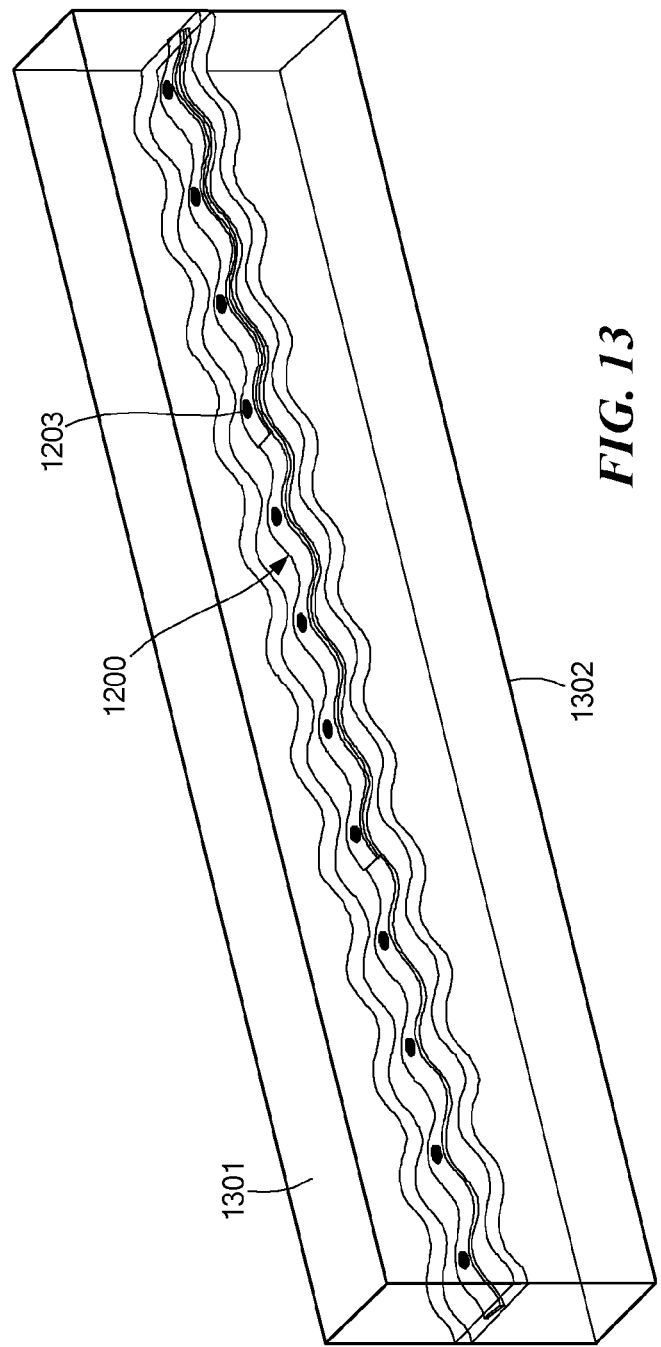
FIG. 12
FIG. 13

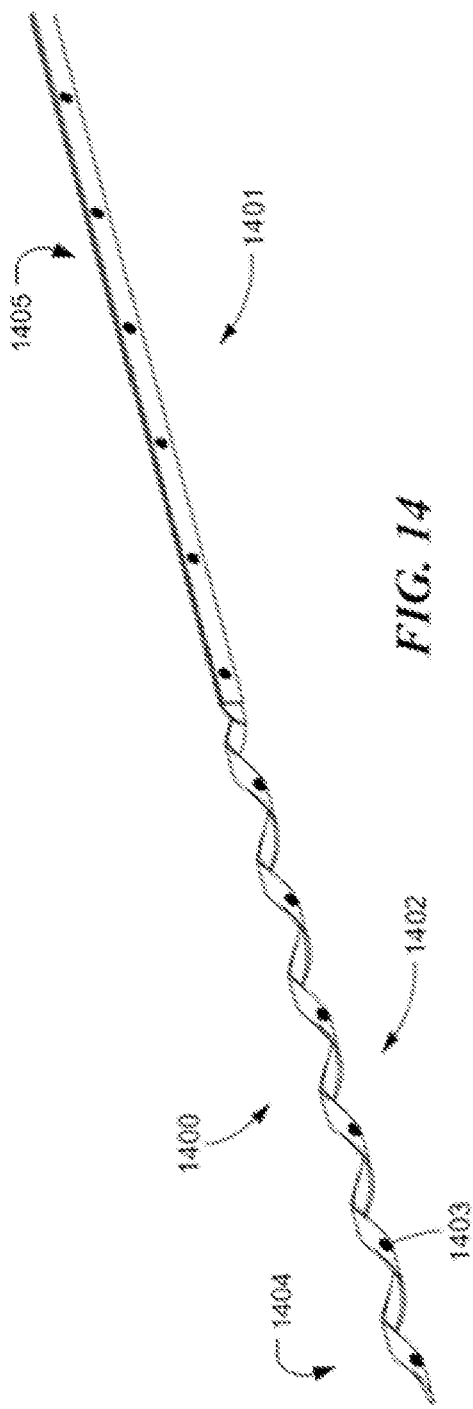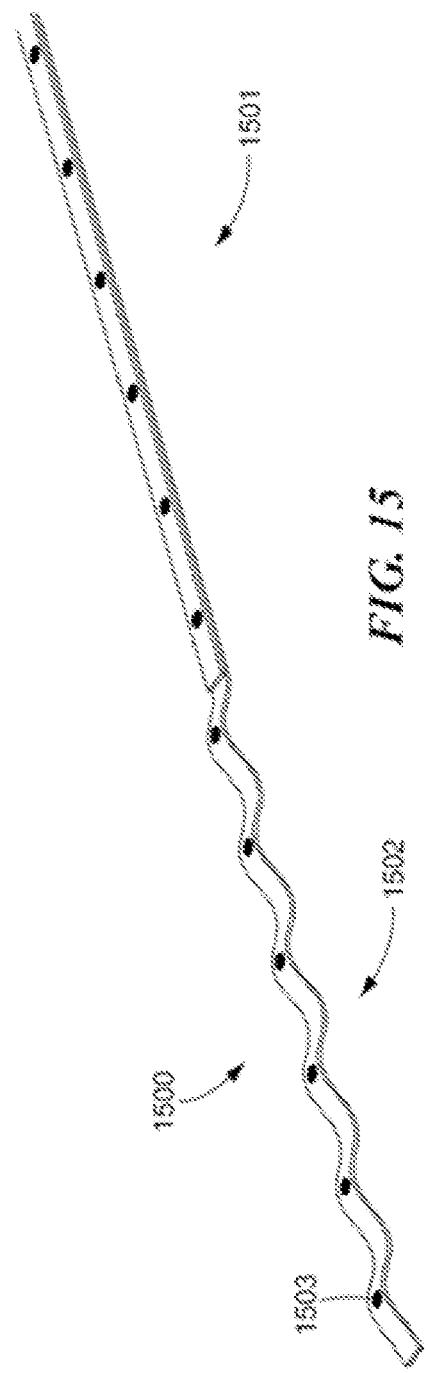

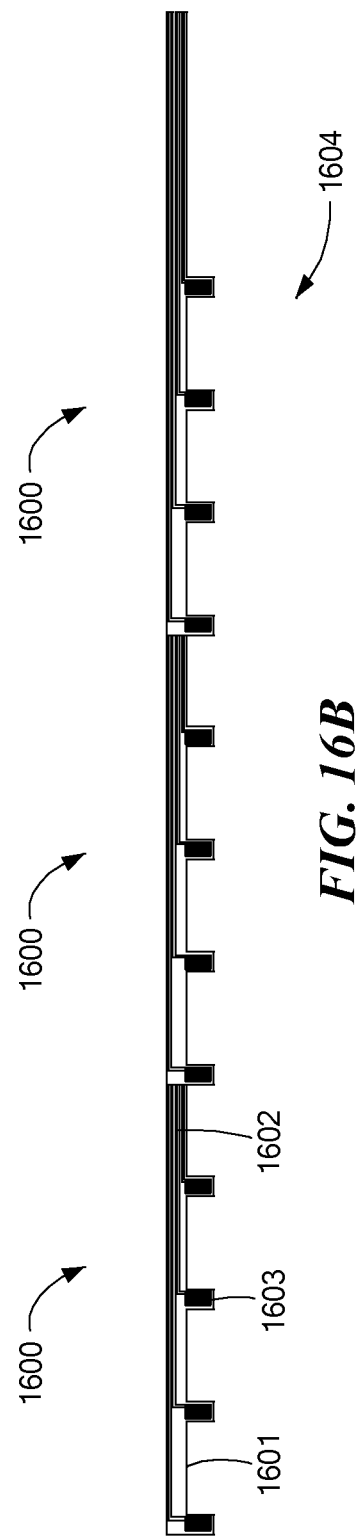

HELICAL CORE EAR IMPLANT ELECTRODE

This application is a continuation of Patent Cooperation Treaty Application PCT/US11/42557, filed Jun. 30, 2011, which claims priority from U.S. Provisional Patent Application 61/359,928, filed Jun. 30, 2010, which are incorporated herein by reference.

FIELD OF THE INVENTION

The present invention relates to medical implants, and more specifically to an implant electrode array used in ear implant systems such as cochlear implants (CI) and vestibular implants (VI).

BACKGROUND ART

A normal ear transmits sounds as shown in FIG. 1 through the outer ear 101 to the tympanic membrane (eardrum) 102, which moves the bones of the middle ear 103 (malleus, incus, and stapes) that vibrate the oval window and round window openings of the cochlea 104. The cochlea 104 is a long narrow duct wound spirally about its axis for approximately two and a half turns. It includes an upper channel known as the scala vestibuli and a lower channel known as the scala tympani, which are connected by the cochlear duct. The cochlea 104 forms an upright spiraling cone with a center called the modiolar where the spiral ganglion cells of the acoustic nerve 113 reside. In response to received sounds transmitted by the middle ear 103, the fluid-filled cochlea 104 functions as a transducer to generate electric pulses which are transmitted to the cochlear nerve 113, and ultimately to the brain.

Hearing is impaired when there are problems in the ability to transduce external sounds into meaningful action potentials along the neural substrate of the cochlea 104. To improve impaired hearing, auditory prostheses have been developed. For example, when the impairment is related to operation of the middle ear 103, a conventional hearing aid may be used to provide acoustic-mechanical stimulation to the auditory system in the form of amplified sound. Or when the impairment is associated with the cochlea 104, a cochlear implant with an implanted electrode contact can electrically stimulate auditory nerve tissue with small currents delivered by multiple electrode contacts distributed along the electrode.

FIG. 1 also shows some components of a typical cochlear implant system which includes an external microphone that provides an audio signal input to an external signal processor 111 where various signal processing schemes can be implemented. The processed signal is then converted into a digital data format, such as a sequence of data frames, for transmission into the implant 108. Besides receiving the processed audio information, the implant 108 also performs additional signal processing such as error correction, pulse formation, etc., and produces a stimulation pattern (based on the extracted audio information) that is sent through an electrode lead 109 to an implanted electrode array 110. Typically, this electrode array 110 includes multiple stimulation contacts 112 on its surface that provide selective stimulation of the cochlea 104.

The electrode array 110 contains multiple electrode wires embedded in a soft silicone body referred to as the electrode carrier. The electrode array 110 needs to be mechanically robust, and yet flexible and of small size to be inserted into the cochlea 104. The material of the electrode array 110 needs to be soft and flexible in order to minimize trauma to neural structures of the cochlea 104. But an electrode array 110 that is too floppy tends to buckle too easily so that the electrode array 110 cannot be inserted into the cochlea 104 up to the desired insertion depth.

Typically, the electrode wires within the electrode array 110 have a homogenous overall shape from one end to the other: either generally straight, repeating coiled loops, or recurring wave shapes. As shown in FIG. 17, the bend radius of the electrode array 110 becomes ever smaller as it is inserted more deeply into the cochlea. So the electrode array 110 should have non-uniform and non-homogeneous mechanical properties (e.g., bending and flexing) to accommodate the complex path that it must take, and also for maintaining biological compatibility with the surrounding tissue of the cochlea 104.

In addition, present cochlear implant (CI) systems possess numerous stimulation contacts 112 along the electrode array 110 for achieving a frequency distribution and resolution that mimics natural human hearing as far as possible. As the technology advances it is likely that an increasing number of frequency bands will need to be supported by the CI systems for providing an even finer pitched hearing. Consequently, more and more wires and stimulation contacts 112 will have to be placed within the electrode array 110, whose dimensions are restricted by the very limited space in the cochlea 104. In general, it can be said that the more channels (i.e. wires and contacts) an electrode array 110 contains, the more rigid it will be due to the higher amount of metal structures within it.

A trade-off needs to be made between a certain stiffness of the electrode array 110 which allows insertion into the cochlea 104 up to the desired insertion depth without the array buckling, and certain flexibility of the electrode array 110 which keeps mechanical forces on the lateral wall of the scala tympani of the cochlea 104 low enough.

Recent developments in CI electrode array designs and surgical techniques are moving towards minimal trauma implantations. For preservation of residual hearing it is of particular importance to preserve the natural intra-cochlear structures. Therefore, the size and mechanical characteristics of the electrode array are critical parameters for the best patient benefit. Some electrode array designs are pre-curved, though a drawback of that approach is that a special electrode insertion tool is needed which keeps the electrode array straight until the point of insertion.

As documented by Erixon et al., *Variational Anatomy of the Human Cochlea: Implications for Cochlear Implantation*, Otology & Neurotology, 2008 (incorporated herein by reference), the size, shape, and curvature of the cochlea varies greatly between individuals, meaning that a CI electrode array must match a wide range of scala tympani (ST) geometries. Furthermore, recently published research by Verbist et al., *Anatomic Considerations of Cochlear Morphology and Its Implications for Insertion Trauma in Cochlear Implant Surgery*, Otology, & Neurotology, 2009 (incorporated herein by reference) has shown that the human ST does not incline towards the helicotrema at a constant rate, but rather there are several sections along the ST where the slope changes, sometimes even becoming negative (i.e. downwards). The location and grade of these changes in inclination were also found to be different from individual to individual. Consequently, CI electrode arrays should be highly flexible in all directions in order to adapt to individual variations in curvature and changes in inclination of the ST for minimal trauma implantation.

Present day CI electrode arrays require considerable amount of hand assembly during manufacturing. Single thin platinum wires covered with a thin electrical insulation must be cut to size and manipulated without compromising the insulation. The wires must be stripped of insulation at the ends and welded to small thin platinum foils that act as stimulation contacts. Each wire must be individually placed inside a mold and assembled in a multi-channel structure before being silicone injection molded. Demolding of long electrodes must take place without causing damage to the structure.

Some rejects inevitably occur during manufacturing due to open or short circuits between wires, or poor welding to the contacts. Silicone overflow on contact surfaces may cause further rejects. The process of making electrodes is extremely labor intensive and a considerable percentage of rejected electrodes is unavoidable since maintenance of acceptable quality is difficult. In addition, the manual work is very operator dependent and difficult to specify in adequate detail to give reproducible results. Hand-made devices may therefore unintentionally and undesirably be subject to significant variations in performance Furthermore, manual work is linked with extensive and time-consuming training of personnel and manual production may in general not be financially competitive.

It would therefore be desirable to have a streamlined method for making implant electrodes using an automated process. The requirements as to number of stimulation channels, size, and mechanical properties constitute a challenging problem for traditional and modern electrode manufacturing techniques. U.S. Pat. No. 6,374,143 by Berrang et al. ("Berrang", incorporated herein by reference) presents a process for fabricating thin-film CI electrodes by encapsulating platinum structures between two polymer films. This process can be automated and thus attempts to address the problem of a lacking streamlined electrode manufacturing as described above. In the same patent, folding is suggested for miniaturization of an electrode array in order to pack the many metal wires into a smallest possible space. U.S. Pat. No. 7,085,605 by Bluger et al. ("Bluger", incorporated herein by reference) discloses a similar method for an implantable medical assembly. WO2008/011721 by Spruit ("Spruit", incorporated herein by reference) proposes stacking of several individual assembly layers for essentially achieving the same compact structure. Other methods for manufacturing a thin-film CI electrode include ink-jet printing of platinum ink onto a polymer film, as suggested by U.S. patent application Ser. No. 12/787,866, filed May 26, 2010 (incorporated herein by reference).

As the number of stimulation channels increases, an increasing number of folded or stacked layers is needed for electrically insulating the conducting metal wires from each other. One basic mechanical property of the described (folded or stacked) assemblies is the highly inhomogeneous bending characteristics in different directions, mainly caused by the geometry of the assembly layers containing the wires. The cross-section of these layers is rectangular in shape and therefore has a preferred bending direction. Existing and suggested CI electrode arrays based on the thin-film technology were therefore designed to be highly bendable in the direction of the ST curvature around the modiolus, but far less flexible in the plane parallel to the modiolus. As explained earlier, these characteristics are generally not desirable in CIs since they should be highly bendable in all directions to lower the risk of implantation trauma.

U.S. Pat. No. 5,964,702 ("Grill", incorporated herein by reference) describes stimulating peripheral nerves using cuff electrodes wound in a helical shape where the stimulation contact surfaces are opened inwards towards the internal lumen of the helical shape. WO93/20887 ("Grill WO", incorporated herein by reference) describes a similar arrangement for thin film implant electrodes. Both Grill methods use a first layer of elastomer that is cured and stretched and then covered by second layer of elastomer so that the different mechanical tensions in the two elastomer layers cause the layered structure to curl into a helix. But in pacemaker electrodes, the size constraints, the number of electrically active channels, and the requirements to flexibility (for preservation of delicate tissues) are fundamentally different than for many specific implant applications such as CI electrodes. It is therefore a challenge to produce CI electrodes that make use of the highly flexible helical shaped wires.

U.S. Patent Publication 2010/0305676 ("Dadd," incorporated herein by reference) describes winding the electrode wires in the extra-cochlear segment of the electrode lead in a helical shape to make that portion of the electrode lead stronger. Dadd is quite clear that such a helical portion does not extend into the intra-cochlear electrode array which needs to be much more flexible than the extra-cochlear lead in order to minimize trauma to the cochlear tissues when the array is inserted.

U.S. Patent Publication 2010/0204768 ("Jolly," incorporated herein by reference) describes winding the individual electrode wires in the intra-cochlear electrode array in an elongated helical shape where each wire is separate and independent.

SUMMARY OF THE INVENTION

Embodiments of the present invention are directed to an electrode array for ear implant systems such as cochlear implants (CI) and vestibular implants (VI). The electrode array includes an electrode array core made of a flexible polymer material including an elongated helical portion having multiple helical turns. Electrode wires are embedded within the array core for carrying electrical stimulation signals. At a terminal end of each electrode wire, an electrode stimulation contact is exposed through the array core for applying the electrical stimulation signals to adjacent neural tissue. An electrode carrier of resilient material encases the electrode array and has an outer surface with contact openings exposing the stimulation contacts.

In further specific embodiments, the helical portion of the array core may include substantially all of the electrode array. Or there may be a second portion of the array core having a substantially planar shape or recurring waves. Or the helical portion of the array core may contain smaller recurring waveform shapes in every helical turn.

In specific embodiments, every helical turn may or may not have a stimulation contact. For example, every second helical turn may have a stimulation contact. There may be a constant or variable distance between helical turns. The helical shape may have a substantially constant diameter or a diameter that decreases towards one end.

Each stimulation contact may be split into multiple contact sections electrically connected by corresponding connecting sections. The stimulation contacts may be formed on contact wings perpendicular to the electrode wires, in which case, the contact wings may be supported by the array core.

BRIEF DESCRIPTION OF THE DRAWINGS

FIG. 2A shows an example of a typical thin-film array core subassembly.

FIG. 2B shows an example of a complete thin-film array core assembly containing multiple subassemblies.

FIG. 3 shows an example of a thin film array core having a helical shape according to an embodiment of the present invention.

FIG. 4 shows an example of helical shaped array core over-molded with a resilient electrode carrier material to form a whole electrode array.

FIG. 5 shows an example of helical shaped array core having a stimulation contact on every other helical turn.

FIG. 6 shows an example of helical shaped array core wherein the spacing between helical turns decreases from one end to the other.

FIG. 7 shows an example of helical shaped array core wherein the helix diameter decreases from one end to the other.

FIG. 8 shows an example of helical shaped array core wherein the stimulation contacts have a trapezoid shape.

FIG. 9 A-D shows an example of helical shaped array core wherein the exposed ends of the electrode wires form the stimulation contacts.

FIG. 10 A-D shows an example of helical shaped array core wherein each stimulation contact is split into contact sections with connecting sections.

FIG. 12 shows an example of a thin film array core having a wavy shape according to an embodiment of the present invention.

FIG. 13 shows an example of molding arrangement for manufacturing a wavy shape thin film array core according to an embodiment of the present invention.

FIG. 14 shows an example of a thin film array core having a helical wound portion and a planar portion.

FIG. 15 shows an example of a thin film array core having a wavy shape portion and a planar portion.

FIG. 16 A-B shows an example of a thin film implant array core having contact wings for stimulation contacts.

DETAILED DESCRIPTION OF SPECIFIC EMBODIMENTS

Figure 1:
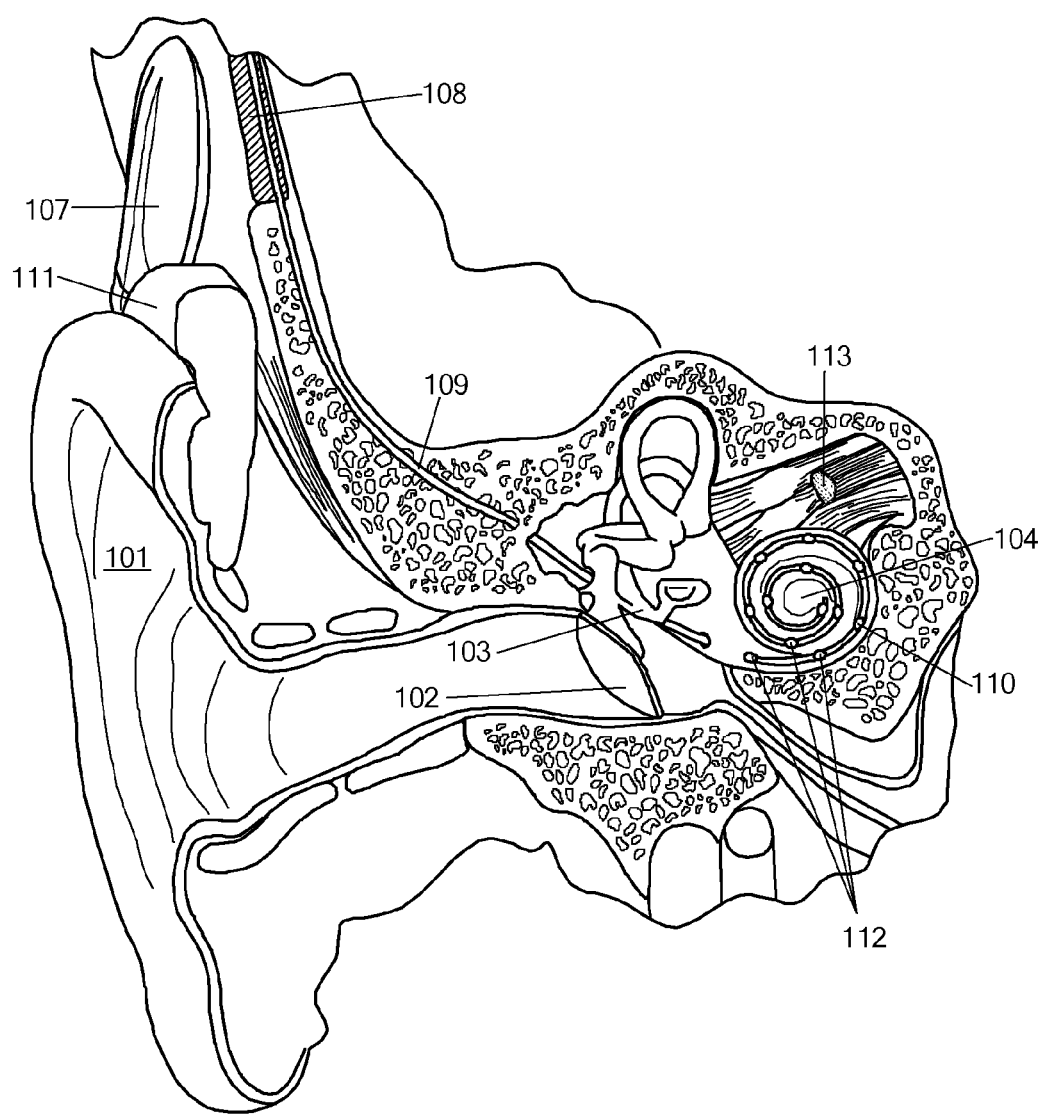
FIG. 1 shows anatomical structures in a human ear having a cochlear implant system.

Embodiments of the present invention are directed to a new electrode array design and a method of manufacturing such an electrode array to overcome some of the disadvantages of previous thin-film electrode arrays Improved flexibility in a planar thin film electrode array can be realized based on several specific array core shapes such as a helical shape and a wavy shape array core. Such shapes improve the flexibility of the planar electrode circuit, which in turn helps preserving tissue when the electrode array is surgically implanted, for example, preserving the cochlear tissue in the cochlea.

The Jolly electrode array described in U.S. Patent Publication 2010/0204768 describes winding the individual wires in the electrode array in a helical shape where each wire is separate and independent. However, the Jolly arrangement is not suitable for use with the thin-film electrode array where the wires are embedded together in a common polymer material that must be manipulated as a single structure. Nor is it easy to simply wind a thin-film electrode array into a helical shape.

As the number of stimulation channels increases, a thin-film electrode array needs an increasing number of folded or stacked layers for electrically insulating the conducting metal wires from each other. One basic mechanical property of the described (folded or stacked) assemblies is the highly non-homogeneous bending characteristics in different directions, mainly caused by the geometry of the assembly layers containing the wires. The cross-section of these layers is rectangular in shape and therefore has a preferred bending direction. Existing and suggested CI electrode arrays based on the thin-film technology were therefore designed to be highly bendable in the direction of the ST curvature around the modiolus, but far less flexible in the plane parallel to the modiolus. As explained earlier, these characteristics are generally not desirable in CIs since they should be highly bendable in all directions to lower the risk of implantation trauma.

Moreover, the conventional approach to forming a thin-film electrode array is to stack the sub-assembly layers, and then heat them to melt the polymer film material into a single structure. But when shaping a planar multi-layered thin-film electrode wiring structure into a helix there will be significant forces acting on the inner and outer layers, especially as the stack grows thicker. This potentially could damage the wiring structures in these layers. That makes such structures unsuitable for use as ear implant electrode arrays.

But embodiments of the present invention are able to overcome these problems. If the stacked sub-assembly layers are wound into a helical shape before bonding the layers together, and then heat treat them to melt the layers together and simultaneously set the helical shape. This change in the production process will leave each of the sub-assembly modules in a comparably stress-free condition that is now workable for use as an intra-cochlear electrode array. This same approach also would for work for other shapes such as wavy shaped structures, etc.

FIG. 2A shows an example of a typical thin-film array core subassembly 200 suitable for specific embodiments of the present invention where a thin film array core 201 encloses the electrode wires 202 while having openings on the outer surface that expose the stimulation contacts 203. FIG. 2B shows an example of a complete thin-film array core assembly 204 containing multiple subassemblies 200. In a complete array core assembly 204, the electrode wires carry the electrical stimulation signals from an implant housing at the base end (the electrode lead) to the stimulation contacts 203 which apply the electrical stimulation signals to target neural tissue. Array core subassemblies 200 and array core assemblies 204 may be produced, for example, as described by Berrang or Jolly and stacked or folded as already described by Spruit and Bluger. The number of array core assemblies 200 used in the complete array core assembly 204 depends on the specific array core design. Size of the stimulation contacts 203 and electrode wires 202 and the number of stimulation channels are primary parameters that determine the number of core sub-assemblies 204 that are needed, but also process limitations such as the placement accuracy of the electrode wires 202 and stimulation contacts 203 with respect to the thin film array core 201 also may play a role.

FIG. 3 shows an example of a thin film array core 300 having a helical shape according to an embodiment of the present invention to obtain the advantage of improved flexibility in all bending directions. The array core 300 has electrode wires 302 embedded within by an elongated planar thin film array core 301. At the end of each electrode wire 302 is a stimulation contact 303. At least a portion of the thin film array core 301 is formed into an elongated helical shape having helical turns that provides the desired improved flexibility. The helical shape of the stacked or folded thin film array core 301 can be realized, for example, by first shaping the core into the desired form by winding around a rod 304 with subsequent thermo-forming heat treatment to permanently fix the shape, or by shaping the core into the desired helical shape and then inserting it into a flexible tube for holding the shape.

FIG. 4 shows an example of helical shaped array core 300 which has been over-molded with a resilient electrode carrier 401 such as biocompatible silicone to form a whole electrode array 400. The silicone material of the electrode carrier 401 establishes a smooth outer surface over the array core 300 to further reduce insertion trauma. The molding of the electrode carrier 401 can be based on injection molding or by insertion of the thin film array core 301 into a silicone support tube. Surface openings in the electrode carrier 401 can be made over the stimulation contacts 303, for example, by masking the stimulation contacts 303 during to the molding process or by post-molding laser or mechanical treatment to selectively remove the silicone carrier material. The silicone electrode carrier 401 also adds some mechanical stability to the highly flexible shaped electrode array 400 to avoid compression and kinking during implantation into the cochlea.

In such an electrode array 400, the bend control elements may be formed by sections of the electrode carrier 401 between the helical turns of the array core 300. The helical structure of the array core 300 may have the desired property of easily bending in the lateral direction due to its helical design. However, the silicone material of the encasing electrode carrier 401 may actually act in the opposing way to resist lateral bending. So if the array core 300 has a high number of helical turns, then the array core 300 easily bends laterally; but at the same time, because there are many helical turns, there is less silicone carrier material between them. So the interstitial silicone material of the electrode carrier 401 between the helical turns of the electrode core 300 is stretched quite substantially and resists the bending force. On the other hand, if the number of helical turns is low, the array core 300 is less flexible and requires greater force to bend laterally, but there also is less resistive force of the silicone material of the electrode carrier 401 because the portion between the helical turns is larger.

While FIG. 3 shows an array core 300 having a number of helical turns and a number of stimulation contacts 303 that are equal, other specific embodiments may be different and it may be that not every helical turn contains a stimulation contact 303. For example, FIG. 5 shows a helical shaped array core 300 having a stimulation contact 303 on every other helical turn. FIG. 6 shows an example of helical shaped array core 300 wherein the spacing between helical turns decreases from one end 601 to the other 602. FIG. 7 shows an example of helical shaped array core 300 wherein the helix diameter decreases from one end to the other. And FIG. 8 shows an example of helical shaped array core 300 wherein the stimulation contacts 303 have a trapezoid shape.

In the foregoing embodiments, the stimulation contacts all are much wider than the electrode wires. FIG. 9 A-D shows an example of another embodiment of an array core 900 wherein the exposed ends of the electrode wires 902 themselves form the stimulation contacts 903. FIG. 9 A shows an electrode subassembly where multiple insulated electrode wires 902 are supported on a thin film array core 901. The terminal ends of the electrode wires 902 are uninsulated and exposed to form the stimulation contacts 903. As shown in FIG. 9 B, multiple electrode subassemblies are arranged in series to form a complete array core 900. The thin film array cores 901 are then thermoformed into a helical shape as shown in FIG. 9 C, and enclosed in resilient electrode carrier material 904 as shown in FIG. 9 D which leaves exposed only the long thin wire ends of the stimulation contacts 903. In specific embodiments, these wire end stimulation contacts 903 may extend over one or more helical turns.

Given the small cross-sectional size of potential insertion sites such as the scala tympani of the cochlea, the curvature of the helical turns must be great enough to allow the electrode array to fit in the desired location without damaging the delicate tissue structures involved. This means that the electrode wires and the stimulation contacts must be significantly deformed from their original planar shape as found in the original subassembly. For large structures such as the stimulation contacts, this bending may be difficult to achieve without damaging the polymer film core and/or the material (such as platinum) of the contact itself.

One solution to this problem is to divide each stimulation contact into two or more smaller sections in the direction of the helical bending with one or more thinner connecting sections that electrically connect the contact sections. Bending will then preferentially occur at these thinner connecting sections and less or not at all in the larger and more rigid contact sections. FIG. 10 A-D shows an example of helical shaped array core 1000 wherein each stimulation contact 1003 is split into contact sections 1004 with one or more connecting sections 1005. In the example shown in FIG. 10, each stimulation contact 1003 is divided into two semi-circular contact sections 1004 with narrow connecting section 1005 at either end. When initially fabricated into an electrode subassembly on a thin film array core 1001 as shown in FIG. 10 C, the stimulation contacts 1003 remain in the planar form of the core. During the electrode shaping process when a group of array core subassemblies is wound into helical form as shown in FIG. 10 D, the connecting sections 1005 bend easily as shown in detail in FIG. 10 B to accommodate the helical shape.

The foregoing examples have a relatively constant amount of flexibility from one end of the electrode array to the other, but that is not necessarily always the case. For example, it is generally desirable that the basal end of the electrode array be stiffer (more rigid) and less flexible than the apical end to improve the surgical handling and avoid kinks or collapses in the electrode during surgical insertion. In addition, the base end should be stiff enough to overcome the frictional forces between the electrode array and the target tissue without kinking. One way to achieve this is by using more layers of the core material towards the base end than the apical end.

Figure 11A:
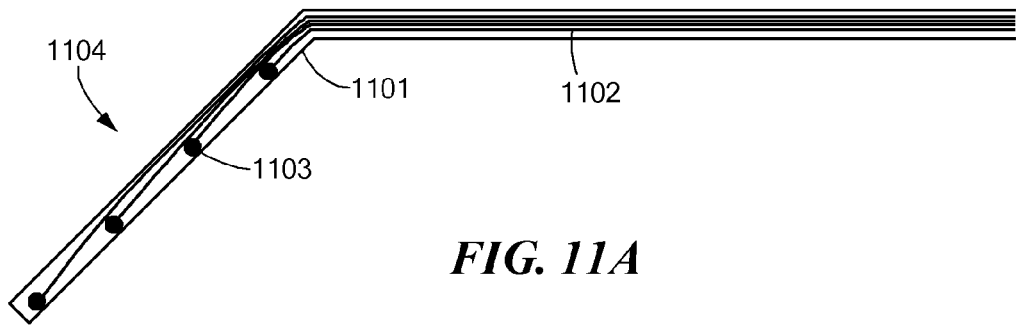
FIG. 11 A-C shows an example of helical shaped array core wherein each array core divides into an angled branch
Figure 11B:
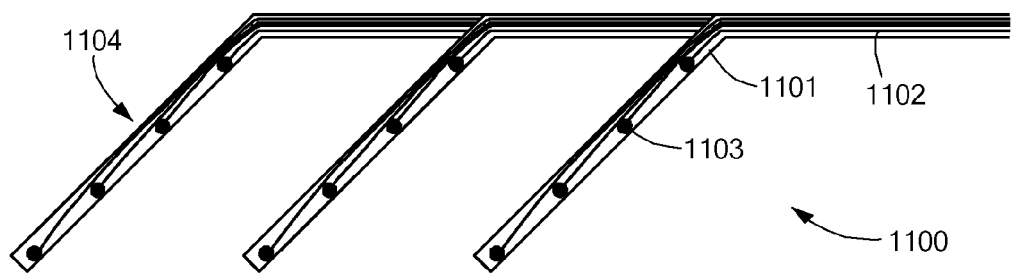
Figure 11C:
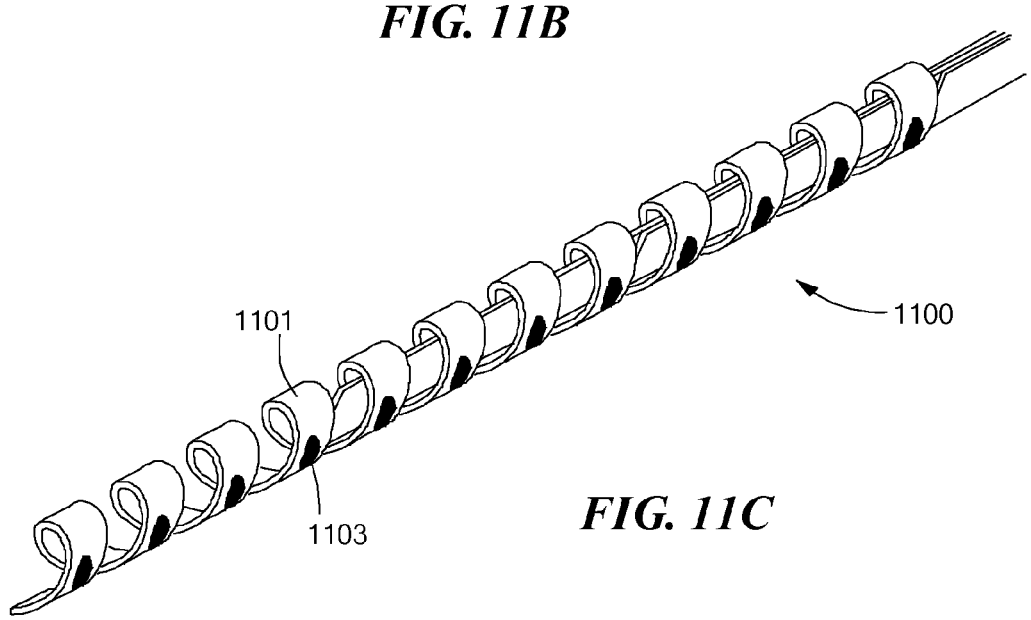

FIG. 11 A-C shows an example of such an array core 1100 based on an electrode array core 1101 that divides into angled branches 1104. FIG. 11 A shows a single array core subassembly wherein the thin film array core 1101 has an angled branch 1104. In FIG. 11 B, three branched array subassemblies are stacked together to form a complete planar form array core 1100. The individual angled branches 1104 can then be helically wound around the straight segments of the array core 1101 which has three layers near the base end, progressively decreasing to two, then one, then no layers towards the apical end of the array core 1100. This layered progression of the straight segments of the core 1101 changes the flexibility of the array core 1100 from relatively rigid near the base end (and consequently easier for the surgeon to manipulate) to maximally flexible at the apical end (minimizing tissue trauma).

The foregoing embodiments describe highly flexible electrode arrays which are all based on a helical shaped thin film array core. However a thin film array core can be formed into other shapes that also provide improved flexibility. For example, FIG. 12 shows an example of an array core 1200 having a thin film array core 1201 formed into a wavy shape having a plurality of recurring waves according to an embodiment of the present invention. U.S. Pat. No. 6,843,870 previously proposed such a wave shape for an implantable cable structure, but this shape has not previously been considered or adapted for an array core for insertion into delicate tissues such as cochlear structures. In the embodiment shown in FIG. 12, the array core 1200 is arranged to have a stimulation contact 1203 positioned on the peak of each wave shape, but other embodiments may be arranged differently, for example, having a stimulation contact 1203 on every other wave or having one portion of the array core 1200 where there are stimulation contacts 1203 on every wave and another portion of the array core 1200 where there are stimulation contacts 1203 on every second wave, etc.

FIG. 13 shows an example of molding arrangement for manufacturing a wavy shape thin film array core 1200 according to an embodiment of the present invention. A planar form of the electrode 1200 in which the core 1201 is made of a thermoformable polymer material is placed in heat treatment mold having complementary wave shaped blocks 1301 and 1302. As the mold blocks 1301 and 1302 are heated, the array core 1201 softens and conforms to the wave shapes of the molds, in which form it then hardens after cooling.

In some embodiments, it may be advantageous to have sections which are shaped differently. For example, FIG. 14 shows an example of a thin film array core 1400 having a helical shape section 1402 towards the apical end 1404 for increased flexibility, and a planar section 1401 at the base end 1405 which is more rigid and therefore easier for the surgeon to handle.

Figure 17:
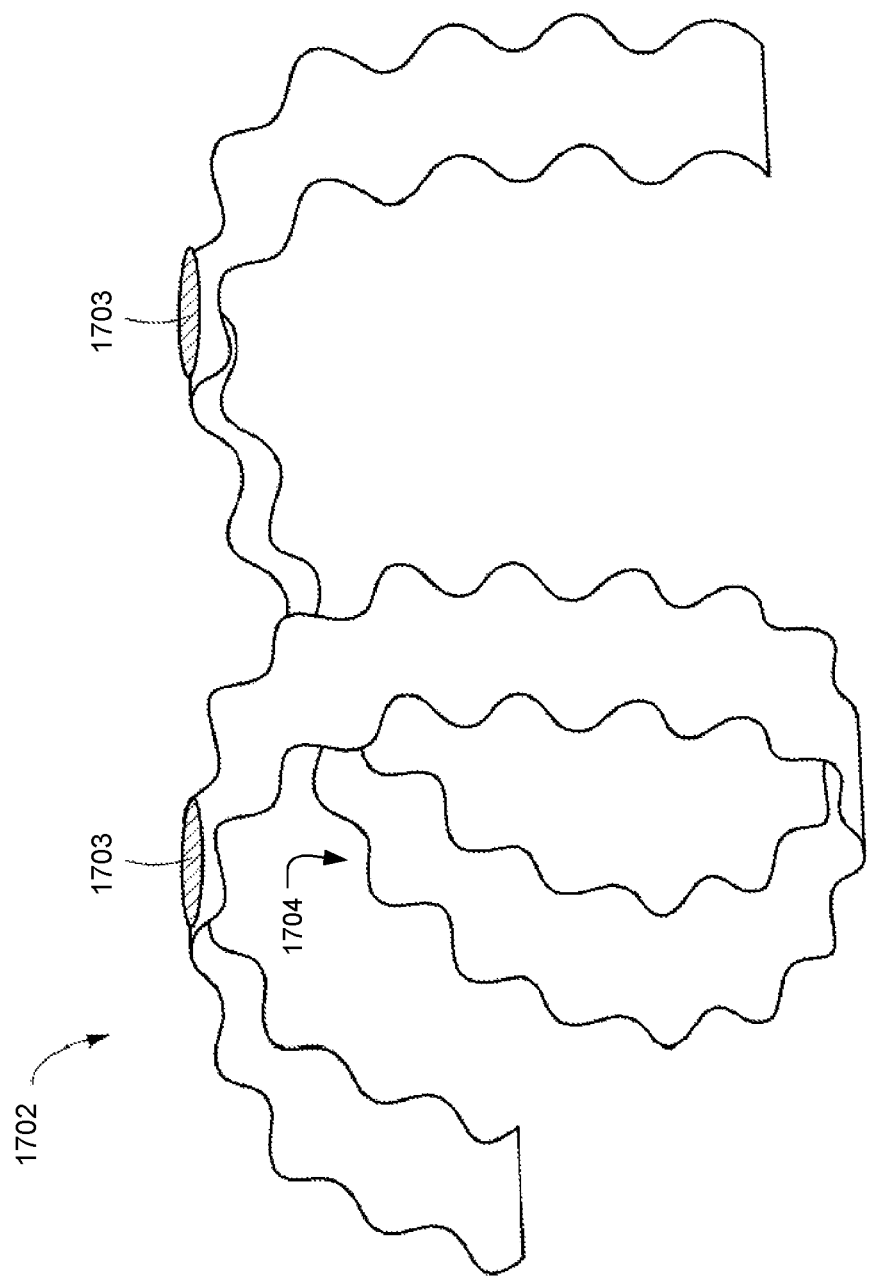
FIG. 17 shows an example of a thin film array core related to the one shown in FIG. 14 having a helical wound portion with a smaller recurring waveform pattern within the core material.

FIG. 17 shows an example of a thin film array core related to the one shown in FIG. 14 having a helical wound portion 1702 between the stimulation contacts 1703 with a smaller recurring waveform pattern 1704 within the thin film material. Such a mixed pattern of a smaller recurring waveform 1704 within a larger helical winding can be shaped by initially stacking the thin film core and heating to some first temperature T1 that softens the thin film and allows it to be shaped into a wave-shape form, and then cooled to maintain the wave-shape. The thin film core can then be heated again to a different temperature T2 (somewhat lower than T1), shaped into the elongated helix form, and then cooled to retain the helix shape with the smaller recurring wave-form 1704.

FIG. 15 shows another similar example of a thin film array core 1500 having a wavy shape section 1502 and a planar section 1501. The embodiments shown in FIGS. 14 and 15 have stimulation contacts 1403 and 1503 respectively on both sections of the array core, which is not necessarily the case in other embodiments, which may have stimulation contacts in just one section, or even just a portion of one section.

The stimulation contacts need to have some minimum area for safe electro-stimulation. In order to reduce the amount (width) of the thin film array core as much as possible (and thereby further increase the flexibility), it may be useful to keep the wire portion of the supporting core as narrow as possible and only increase the assembly width with protrusions at the stimulation contacts. FIG. 16 A-B shows an example of another form of a thin film array core based on using contact wings for stimulation contacts. FIG. 16 A shows an electrode subassembly 1600 having multiple electrode wires 1602 supported by a thin film array core 1601 which includes lateral protrusions that support the contact wing stimulation contacts 1603. FIG. 16 B shows an entire array core 1604 formed of multiple layered subassemblies 1600. Such an arrangement of contact wings minimizes the amount of polymer film core 1601 used, thereby increasing flexibility of the resulting array core 1604. Such an array core may be used in the various ways and forms previously described.

Although various exemplary embodiments of the invention have been disclosed, it should be apparent to those skilled in the art that various changes and modifications can be made which will achieve some of the advantages of the invention without departing from the true scope of the invention.

What is claimed is:

1. An intracochlear electrode array configured to be implanted within the cochlea of an implanted patient, the electrode array comprising:
    an electrode array core comprising a plurality of thin-film layers of a flexible polymer material, the electrode array core having an apical end and a base end and including:
        i. a first portion towards the apical end having an elongated helical shape with the plurality of thin-film layers configured to form a plurality of helical turns without residual stress, and
        ii. a second portion towards the base end configured to have a straight planar shape;
    a plurality of electrode wires embedded within the array core for carrying electrical stimulation signals;
    at a terminal end of each electrode wire, an electrode stimulation contact exposed through the array core for applying the electrical stimulation signals to adjacent neural tissue; and
    an electrode carrier of resilient material encasing the electrode array and having an outer surface with a plurality of contact openings exposing the stimulation contacts;
    wherein the material of the electrode carrier and the helical turns of the first portion of the electrode array core are configured to cooperate to provide flexibility for lateral bending during insertion of the electrode array into the cochlea of the implanted patient; and
    wherein he material of the electrode array and the straight planar shape of the second portion of the electrode array core are configured to cooperate to provide rigidity that requires increased lateral bending force for handling by a surgeon implanting the electrode array into the cochlea of the implanted patient.

2. An implantable electrode array according to claim 1, wherein the helical portion of the array core contains a plurality of smaller recurring waveform shapes in every helical turn in the first portion of the electrode array core.

3. An implantable electrode array according to claim 1, wherein every helical turn in the first portion of the electrode array core has a stimulation contact.

4. An implantable electrode array according to claim 1, wherein not every helical turn in the first portion of the electrode array core has a stimulation contact.

5. An implantable electrode array according to claim 4, wherein every second helical turn in the first portion of the electrode array core has a stimulation contact.

6. An implantable electrode array according to claim 1, wherein the electrode array has a constant distance between helical turns in the first portion of the electrode array core.

7. An implantable electrode array according to claim 1, wherein the electrode array has a variable distance between helical turns in the first portion of the electrode array core.

8. An implantable electrode array according to claim 1, wherein the helical shape has a constant diameter.

9. An implantable electrode array according to claim 1, wherein the helical shape has a diameter that decreases towards one end.

10. An implantable electrode array according to claim 1, wherein each stimulation contact is split into a plurality of contact sections electrically connected by a plurality of connecting sections.

11. An implantable electrode array according to claim 1, wherein the stimulation contacts are formed on contact wings perpendicular to the electrode wires.

12. An implantable electrode array according to claim 11, wherein the contact wings are supported by the array core.

* * * * *